US010578561B2

(12) United States Patent
San Martin et al.

(10) Patent No.: US 10,578,561 B2
(45) Date of Patent: Mar. 3, 2020

(54) SELECTIVE PIPE INSPECTION

(71) Applicant: Halliburton Energy Services, Inc., Houston, TX (US)

(72) Inventors: Luis Emilio San Martin, Houston, TX (US); Reza Khalaj Amineh, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 135 days.

(21) Appl. No.: 15/125,720

(22) PCT Filed: Nov. 24, 2015

(86) PCT No.: PCT/US2015/062276
§ 371 (c)(1),
(2) Date: Sep. 13, 2016

(87) PCT Pub. No.: WO2017/091204
PCT Pub. Date: Jun. 1, 2017

(65) Prior Publication Data
US 2018/0017508 A1 Jan. 18, 2018

(51) Int. Cl.
*G01N 22/02* (2006.01)
*E21B 47/00* (2012.01)
(Continued)

(52) U.S. Cl.
CPC ............. *G01N 22/02* (2013.01); *E21B 47/00* (2013.01); *G01B 15/02* (2013.01); *G01R 27/02* (2013.01);
(Continued)

(58) Field of Classification Search
CPC ..... G01N 22/02; G01R 33/1223; G01B 15/02
See application file for complete search history.

(56) References Cited

U.S. PATENT DOCUMENTS 5,926,024 A * 7/1999 Blount ................. G01N 22/00
324/324
9,803,466 B2 * 10/2017 Donderici ........... E21B 47/0006
(Continued)

FOREIGN PATENT DOCUMENTS

EP 0332048 A2 * 9/1989 .......... G01N 27/904
EP 0332048 A2 9/1989
(Continued)

OTHER PUBLICATIONS

"International Application Serial No. PCT/US2015/062276, International Search Report dated Aug. 24, 2016", 3 pgs.
(Continued)

*Primary Examiner* — Manuel A Rivera Vargas
*Assistant Examiner* — Yaritza H Perez Bermudez
(74) *Attorney, Agent, or Firm* — Gilliam IP PLLC

(57) ABSTRACT

A method, apparatus, and system operate to include transmitting a plurality of electromagnetic waves, over a range of frequencies, into a plurality of pipes. The secondary electromagnetic field responses, associated with the electromagnetic waves, from the plurality of pipes are measured. Selective ones of the secondary electromagnetic field responses are canceled or reduced based on a selected pipe for inspection of the plurality of pipes.

17 Claims, 6 Drawing Sheets

(51) Int. Cl.
*G01V 3/26* (2006.01)
*G01V 3/18* (2006.01)
*G01V 3/28* (2006.01)
*G01B 15/02* (2006.01)
*G01R 27/02* (2006.01)
*G01R 33/12* (2006.01)
*E21B 47/18* (2012.01)

(52) U.S. Cl.
CPC ........... *G01R 33/1223* (2013.01); *G01V 3/18* (2013.01); *G01V 3/26* (2013.01); *G01V 3/28* (2013.01); *E21B 47/18* (2013.01)

(56) References Cited

U.S. PATENT DOCUMENTS

| | | | |
|---|---|---|---|
| 2003/0025497 A1 | 2/2003 | Collingwood et al. | |
| 2003/0173959 A1* | 9/2003 | Paulson | G01N 27/82 324/220 |
| 2005/0046589 A1* | 3/2005 | Wisler | E21B 17/003 340/854.6 |
| 2011/0209540 A1* | 9/2011 | Banks | E21B 29/00 73/152.16 |
| 2013/0193953 A1* | 8/2013 | Yarbro | E21B 47/082 324/76.77 |
| 2015/0378046 A1* | 12/2015 | Donderici | E21B 47/0002 324/339 |
| 2016/0069842 A1* | 3/2016 | Bonavides | G01N 29/225 73/152.03 |
| 2016/0168975 A1* | 6/2016 | Donderici | E21B 47/0006 324/238 |
| 2017/0261469 A1* | 9/2017 | Chang | E21B 47/00 |
| 2018/0259671 A1* | 9/2018 | San Martin | E21B 47/0002 |

FOREIGN PATENT DOCUMENTS

| | | | | |
|---|---|---|---|---|
| EP | 0816838 A1 * | 1/1998 | ........... | E21B 47/082 |
| EP | 0816838 A1 | 1/1998 | | |
| WO | WO 2012103541 A2 * | 8/2012 | .......... | G01M 5/0025 |
| WO | WO-2012103541 A2 | 8/2012 | | |

OTHER PUBLICATIONS

"International Application Serial No. PCT/US2015/062276, Written Opinion dated Aug. 24, 2016", 10 pgs.

* cited by examiner

US 10,578,561 B2

SELECTIVE PIPE INSPECTION

PRIORITY APPLICATIONS

This application is a U.S. National Stage Filing under 35 U.S.C. § 371 from International Application No. PCT/US2015/062276, filed on Nov. 24, 2015, which application is incorporated herein by reference in its entirety.

BACKGROUND

Hydrocarbon production may use metal pipes, disposed in a geological formation, for bringing the hydrocarbons to the surface. Since hydrocarbon production may last for years or even decades, it is desirable to monitor the status of the metal pipes to ensure that corrosion has not degraded zonal isolation and improve production.

DETAILED DESCRIPTION

Some of the challenges noted above, as well as others, can be addressed by performing measurements at multiple frequencies in order to derive individual thicknesses, permeability, and other properties of pipes. By selectively reducing or canceling responses from certain pipes, the remaining responses from certain desired pipes may be better evaluated.

In the interest of clarity and brevity, subsequent reference is made to pipes. However, the examples disclosed here work equally well with any metal structure such as metal casings. Thus, the term "pipe" is used to refer to pipes, casings, or other metal structures.

Figure 1:
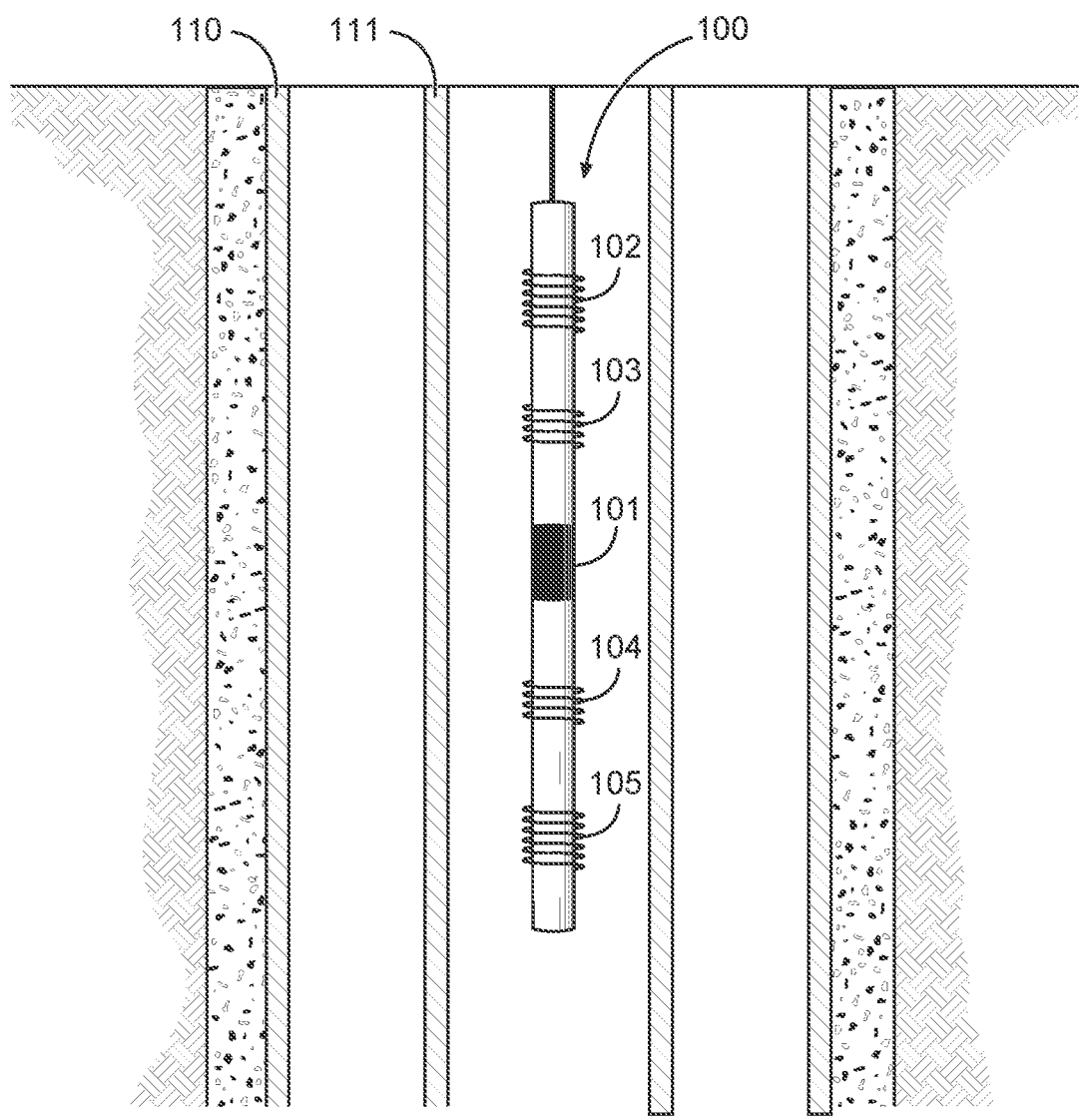
FIG. 1 is a diagram showing an inspection tool in a system of pipes, according to various examples of the disclosure.

FIG. 1 is a diagram showing an inspection tool 100 in a system of pipes 110, 111, according to various examples of the disclosure. The inspection tool 100 is for purposes of illustration only as other tools may be used to accomplish substantially similar results.

The inspection tool 100 includes one or more excitation sources 101 (e.g., transmitters) and one or more receivers 102-105 (e.g., antennas). The inspection tool 100 may be disposed in a wireline tool (see FIG. 4). The receivers 102-105 are spaced apart from the one or more transmitter(s) 101 by a distance s.

In an example, the transmitter 101 may be an electromagnetic excitation source that transmits an electromagnetic wave through the various pipes 110-111 and geological formation. The electromagnetic wave may have a frequency range from approximately 0.1 Hertz into the multiple kilohertz range (e.g., 10 kHz). Lower frequencies may be used to enable the electromagnetic wave to reach pipes that are further, in a radial direction, from the transmitter 101. The higher frequencies may be used for inspection of pipes that are closer to the transmitter 101.

The receivers 102-105 may be an axially distributed receiver array 102-105 and provide reception of secondary magnetic field responses from the one or more pipes 110-111 as a result of the original electromagnetic wave generated by the transmitter 101.

Other examples may use other inspection tool 100X architectures. In an example, the tool may have only one transmitter 101 and one receiver 103. In another example, the tool 100 may have one or more transmitter(s) 101 and multiple receivers 102-105 disposed axially along the tool 100, perhaps symmetrically about the transmitter(s) 101.

In operation, the transmitter 101 transmits a sinusoidal signal, in the form of an electromagnetic wave, radially outward through the pipes 110-111. When the electromagnetic wave hits one or more of the pipes 110-111, an eddy current is created in each pipe that experiences the electromagnetic wave. The eddy current produces a secondary magnetic field response that is picked up by the receivers 102-105 over a particular time period. Each response is associated with a different pipe at a respective received frequency. Any defect(s) in the one or more pipes 110-111 has an effect on the secondary magnetic field from that particular pipe. The illustrated inspection tool architecture can generate differential signals sensitive to defects in the pipes. This may be achieved by subtracting signals obtained at receivers symmetrically disposed on the tool 100 with respect to the transmitter 101. The method described herein can be applied to differential signals, non-differential signals, or any tool operating in the frequency domain.

Various operations may be applied to the acquired raw responses prior to any further processing. For example, the received responses may be filtered to reduce noise; averaged by multiple sensors to reduce noise, differences between responses determined or ratios of multiple voltages determined in order to remove unwanted effects (e.g., common voltage drift due to temperature or other temperature correction schemes such as a temperature correction table), calibration to known parameter values from an existing well log, and/or array processing (software focusing) of the responses to achieve different depth of detection or vertical/azimuthal resolution.

The transmitter 101 can emit a multiplicity of frequencies with the purpose of taking different measurements of the pipe configuration. The attenuation across pipes is captured with a parameter called skin depth, which is an approximation valid in this regime of operation. The skin thickness, represented by $\delta$, may be defined as: $\delta\sqrt{=(2/\omega\mu\sigma)}$ where $\omega$ is the angular frequency, $\mu$ is the magnetic permeability and $\sigma$ is the electrical conductivity. The magnitude of the signal received at the inspection tool 100 is proportional to $e^{-2x/\delta}$, where x represents the overall thickness of the metal pipes. In other words, the higher the frequency of the transmitted signal, the greater the attenuation of the received responses at the tool 100. Thus, due to this attenuation in the pipes at higher frequencies, it may be desirable to use relatively low frequencies (e.g., <200 Hz).

A number of different frequencies may be used to interrogate the concentric pipes 110, 111 at different radial depths from the inspection tool 100, according to their different attenuations. The relatively large attenuation across a metal pipe wall implies that the sensitivity to the $2^{nd}$, $3^{rd}$ or other radially deeper pipes becomes smaller. It may be desirable to selectively remove specific pipe contributions, in a multiple pipe configuration, to a received signal at the inspection tool 100 and thus be able to more easily detect possible changes in pipe thicknesses due to corrosion or other defects.

For example, the innermost pipe 111 may correspond to a production pipe and have a relatively small diameter. Since it has the smaller diameter, the inner most pipe 111 generates the largest signal. It may be desirable to reduce the inspection tool's sensitivity to this signal and increase its sensitivity to the other pipes. In other examples, it may be desirable to remove the contributions of other pipes, besides the innermost pipe, in a multiple pipe configuration. A method to improve sensitivity to any particular pipe of a multiple pipe configuration, as disclosed herein, may be used in a pipe inspection operation.

In a method for selective pipe inspection that improves sensitivity to selected pipes being inspected, it is assumed that the measurement is being performed at multiple frequencies. For example, if the characterization is being performed for M concentric pipes, measurements are performed at N frequencies of $f_1$ to $f_N$ (N>M). The following method also assumes that the first known defects are in pipes 1 to M, with M=N+1. In this situation, the responses comprising the N frequencies may include indications of the defects in all pipes emitting a response.

In order to achieve greater sensitivity to the first pipe (i.e., pipe 1), for example, the effects of responses to defects on pipes 2 to M may be reduced or removed from the received signal. This is performed by solving a system of equations, as shown below:

$$\begin{cases} V_2(f_1) + A_1^{(1)} V_2(f_2) + \ldots + A_N^{(1)} V_2(f_N) = 0 \\ \vdots \\ V_M(f_1) + A_1^{(1)} V_M(f_2) + \ldots + A_N^{(1)} V_M(f_N) = 0 \end{cases} \quad (1)$$

where each equation corresponds to a condition of insensitivity to a defect in one of the pipes from 2 to M. In the following system of N equations and N unknowns, a solution for cancellation coefficients (i.e., weights) can be found. Here $V_a(f_b)$ represents the signal due to a defect on the $a^{th}$ pipe at $b^{th}$ frequency.

It is noted that, although the equations below are written for different frequencies, it is possible to use any combination of frequencies and/or transmitter/receiver spacings. In such an example, a signal due to a defect on the $a^{th}$ pipe may be represented by $V_a(f_b,s_c)$, where $f_b$ represents the frequencies, (b=1–N) and $s_c$ represents the spacings (c=1–P, where P is the maximum number of spacings). This produces (M−1)×M×P equations.

Signal $V_a(f_b)$ can be calculated, through simulations or experimentation, by $V_a(f_b)=Vd_a(f_b)-Vnd_a(f_b)$, where $Vd_a(f_b)$ represents the total signal with the defect and $Vnd_a(f_b)$ represents the total signal without the defect. $Vnd_a(f_b)$ may be determined from the well plan.

In order to calibrate the signals, a pre-processing operation may be applied to the signals $V_a(f_b)$, $Vd_a(f_b)$, or $Vnd_a(f_b)$. For example, a ratio of two frequencies $V_a(f_{b1})/V_a(f_{b2})$ may be used instead of individual frequencies $V_a(f_b)$.

In a normal mode of operation, pipe information from a well plan may be used to calculate the $V_a(f_b)$s in Eq. (1). In another example using a differential mode of operation, pipe information from the previous depth may be used to calculate $V_a(f_b)$s for a current depth. This may enable the method to automatically adapt to different pipe properties (which may differ from the well plan) and focus only on the changes that are due to defects. This may lead to response signals that are proportional to changes.

In the system of equations represented by Eq. (1), the first equation corresponds to the situation in which pipe 2 has a defect and the other pipes have no defects. Analogous conditions apply to the intermediate pipes until the last equation that corresponds to the case where pipe M has a known defect and the other pipes have no defects. From this system of equations, the coefficients used to make the received responses selectively insensitive to the defects in pipes 2 to M may be determined. The result of this procedure is a function $F^{(1)}=V(f_1)+A_1^{(1)}V(f_2)+ \ldots +A_N^{(1)}V(f_N)$ that satisfies the condition in Eq. (1) and, therefore, is insensitive to the defects in pipes 2 to M. The same procedure may be applied to obtain a function $F^{(2)}$ that represents a response signal sensitive to pipe 2 and insensitive to responses from all the other pipes. The derivation is analogous the one just described. Such a function may be written as $F^{(2)}=. V(f_1)+A_1^{(2)}V(f_2)+ \ldots +A_N^{(2)}V(f_N)$. The same procedure may be used for any other pipes in the system of pipes. The received response from the last pipe may be represented by $F^{(M)}=V(f_1)+A_1^{(M)}V(f_2)+ \ldots +A_N^{(M)}V(f_N)$.

An example, using the two concentric pipes 110-111 of FIG. 1, may be illustrated using the above-described method. For purposes of illustration of this example only, it is assumed that three different frequencies are transmitted.

In this example, the function F expressed in Eq. (2) below is found such that its sensitivity to the defects on pipe 2 is much higher than the sensitivity of responses of each of the frequencies to defects on pipe 2:

$$F=V_2(f_1)+A_1^{(2)}V_2(f_2)+A_2^{(2)}V_2(f_3) \quad (2)$$

Two coefficients $A_1^{(2)}$ and $A_2^{(2)}$ are initially found by employing the responses due to the two defects of different sizes on pipe 1 at three frequencies and setting F=0 for those defect responses. The functions thus derived display selective cancellation of responses from other pipes.

In another example, the collars of each pipe may be used to find the coefficients that reduce or eliminate that respective collar's response. Once the coefficients that reduce the collar's responses are found, the functions thus derived now have the properties described above. In other words, each function may display selective sensitivity to one particular pipe.

In a logging example (i.e., FIG. 4), the number of resulting equations in the system of equations may be larger than the number of unknowns by imposing conditions on a window of data taken over an interval of logging depth. In such a scenario, the system of equations may be solved by application of least squares methods.

This method may also incorporate known information about the defects present in the first pipe. For example, if information (e.g., wall thickness, defects, diameter) about the first pipe is available, then it could be used to improve the sensitivity of all the other pipes by using the above-described method.

Due to the non-linearity of the response measurements, the selective cancellation may be more useful for the defects used in the derivation of the coefficients and not for defects of arbitrary size. However, the selective cancellation of defects of arbitrary size may be improved by using additional frequencies beyond the three assumed for the above example. For each additional frequency, a new condition corresponding to a defect of a different size may be used.

To describe such a method, another example of a two pipe system 110, 111, such as illustrated in FIG. 1, is described.

This example assumes a single transmitter and a single receiver disposed within the inspection tool 100. Such a tool 100 may be envisioned by removal of receivers 102, 104, 105 from the inspection tool 100 of FIG. 1. The transmitter 101 is assumed to be transmitting three different frequencies.

In this example, the function F expressed in Eq. (3) is found such that its sensitivity to the defects on the outer pipe 110 is much higher than the sensitivity of responses of each of the frequencies to defects on the outer pipe 110:

$$F=V_2(f_1)+A_1^{(2)}V_2(f_2)+A_2^{(2)}V_2(f_3) \quad (3)$$

Initially, two cancellation coefficients, $A_1^{(2)}$ and $A_2^{(2)}$, are found by employing the responses due to two defects of different sizes on the inner pipe 111 at three different frequencies and setting F=0 for those defects. The responses due to the defects are determined for a nominal thickness of the outer pipe 110 and two defect sizes for the inner pipe 111. The nominal thickness of the inner pipe 111 is assumed to be the same as the outer pipe. The relative variation of the function. F, is then evaluated for various defects on the outer pipe 110 with respect to the defect on the outer pipe 110. The sensitivity of the function F would then be higher compared with the sensitivity of the responses at each frequency alone.

Another example illustrates the method for improving sensitivity to selected pipes as applied to more than two pipes (e.g., four pipes). In this example, the effects of responses to defects on pipes 1-3 are reduced or eliminated when evaluating response to defects on the fourth pipe. This is performed by measuring the pre-known responses on pipes 1 to 3, denoted by $V_1$ to $V_3$, at least for four frequencies $f_1$ to $f_4$. These measurements provide the following system of equations:

$$\begin{cases} V_1(f_1) + A_1^{(4)}V_1(f_2) + A_2^{(4)}V_1(f_3) + A_3^{(4)}V_1(f_4) = 0 \\ V_2(f_1) + A_1^{(4)}V_2(f_2) + A_2^{(4)}V_2(f_3) + A_3^{(4)}V_2(f_4) = 0 \\ V_3(f_1) + A_1^{(4)}V_3(f_2) + A_2^{(4)}V_3(f_3) + A_3^{(4)}V_3(f_4) = 0 \end{cases} \quad (4)$$

The coefficients $A_1^{(4)}$ to $A_3^{(4)}$ are then estimated by solving the system of equations illustrated of Eq. (4). Once these coefficients are determined, the resulting function is illustrated in Eq. (5):

$$F=V_4(f_1)+A_1^{(4)}V_4(f_2)+A_2^{(4)}V_4(f_3)+A_3^{(4)}V_4(f_4) \quad (5)$$

The function of Eq. (5) has more sensitivity to the features on the fourth pipe compared to the responses at each frequency ($V_4(f_1)$, $V_4(f_2)$, $V_4(f_3)$, $V_4(f_4)$).

Data acquisition may be accomplished at more frequencies or more pre-known defects than is described herein. In a general, the number of equations can be more than the number of unknowns when solving for the cancellation coefficients $A_1^{(m)}$ to $A_N^{(m)}$. This may occur when measurements are performed for additional pre-known defects or acquired data at additional frequencies. In such an example, the system of equations may be solved using a least square method. Once the coefficients $A_1^{(m)}$ to $A_N^{(m)}$ are estimated, they may be applied to the measured responses in order to characterize the features on the $m^{th}$ pipe by selectively eliminating the effects of the features on the other pipes.

Another example may use selective sensitivity to magnetic permeability changes of different pipes. Such a method may be used to derive functions that display reduced sensitivity to variations in magnetic permeability of the different pipes. In this case, a coefficient may be derived by numerical simulation that focuses on finding the combinations that are most insensitive to changes in magnetic permeability of the pipes. Conditions for selective cancellation of responses may be imposed for changes in magnetic permeability. By using this method, an improved inversion of magnetic permeability of the different pipes can be achieved.

Yet another example may use selective sensitivity to electrical conductivity changes of different pipes. Such a method may be used to derive functions that display reduced sensitivity to variations in electrical conductivity of the different pipes. In this case, the coefficient may be derived by numerical simulation that focuses on finding the combinations that are most insensitive to changes in electrical conductivity of the pipes. Conditions for selective cancellation of responses may be imposed for changes in electric conductivity. By using this method, an improved inversion of electrical conductivity of the different pipes may be achieved.

In the above-described examples, the selective cancellation coefficients may be determined by measuring pre-known features of the pipes. These can be done through simulation of pre-known defects, measurement of pre-known defects in a laboratory environment, or measurements using collars during a logging process since the collars provide repetitive and strong responses during the logging. Another advantage of using collar responses is that the selective cancellation coefficients are evaluated in realistic measurement conditions and for realistic properties of the pipes, including all real parameters of the pipes.

Also in the above-described examples, defects may be determined using an order from inner-most pipes to outer-most pipes. For example, when characterizing two pipes, the defects on the first pipe may be first determined via using electromagnetic or non-electromagnetic techniques. Once the dimensions of the defect(s) on the first pipe are known, the corresponding selective cancellation coefficient may be used from a previously constructed library to improve the sensitivity of the synthesized function F to the defects of the second pipe.

Figure 2:
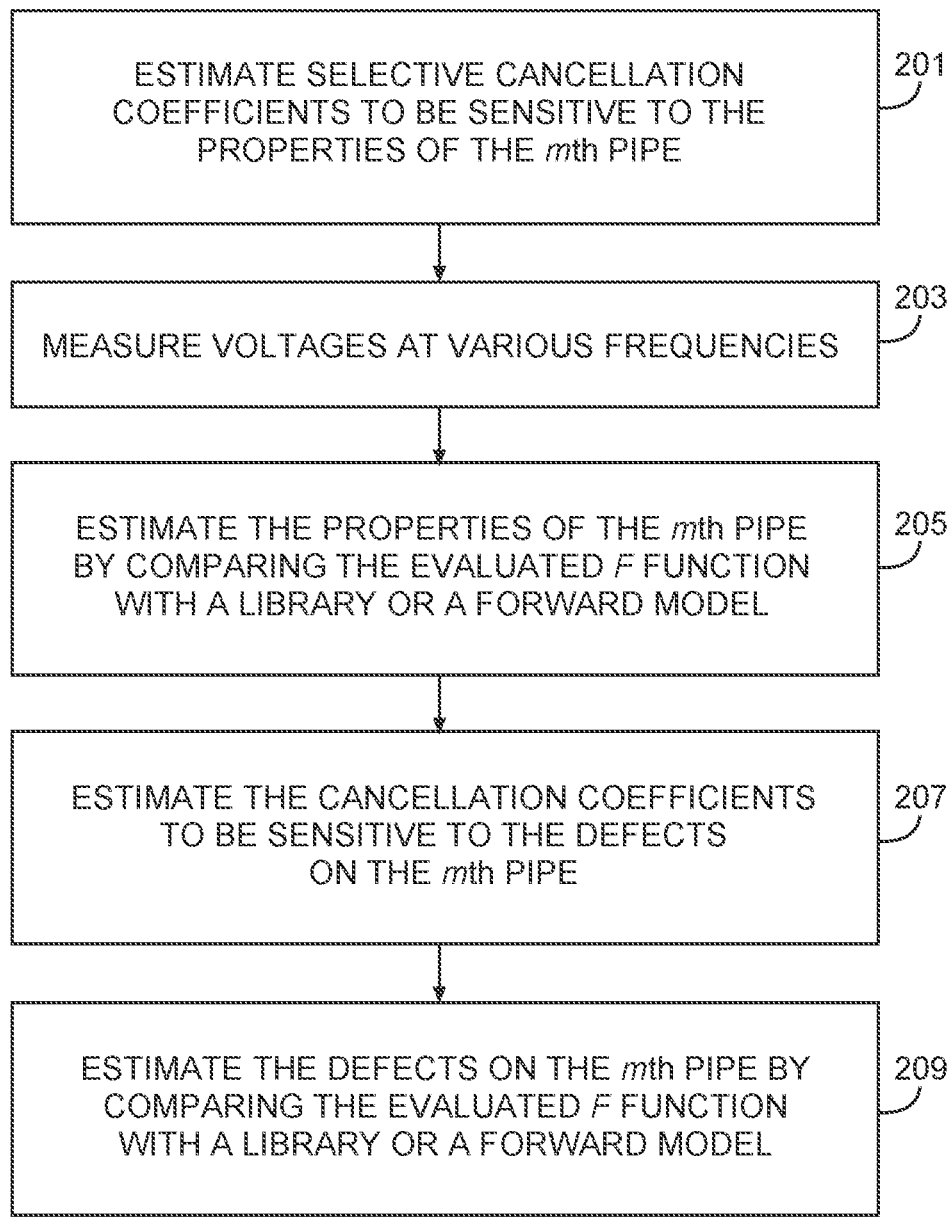
FIG. 2 is a flowchart of a method for an inversion operation for selective cancellation of responses, according to various examples of the disclosure.

FIG. 2 is a flowchart of a method for an inversion operation for selective cancellation of responses, according to various examples of the disclosure. This inversion approach assumes the pipe properties (with fixed, nominal pipe thicknesses) have already been estimated.

Thus, in block 201, the inversion operation estimates the cancellation coefficients (i.e., weights) that are sensitive to the properties of the $M^{th}$ pipe. In block 203, the voltage responses for all frequencies are measured.

Estimates of the values of properties can be obtained by using the same inversion approach applied for assessing the defects. The coefficients $A_1^{(M)}$ to $A_N^{(M)}$ are estimated to increase the sensitivity of the function F to the property change on the $M^{th}$ pipe, perhaps to a maximum value. The measured responses are employed to build the value of the function described above as:

$$F=V(f_1)+A_1^{(m)}V(f_2)+ \ldots +A_N^{(m)}V(f_N) \quad (6)$$

In block 205, the properties of the $M^{th}$ pipe are estimated based on a comparison of the evaluated F function with a library of pipe properties or a simulation model that is built based on the known coefficients $A_1^{(M)}$ to $A_N^{(M)}$. Based on this comparison, the defect(s) on pipe M can be evaluated.

In block 207, the cancellation coefficients that are sensitive to the defect(s) of the $M^{th}$ pipe may be estimated. In block 209, the defects on the $M^{th}$ pipe are estimated by comparison of the evaluated F function (Eq. 6) with the F function library or forward simulation model.

Figure 3:
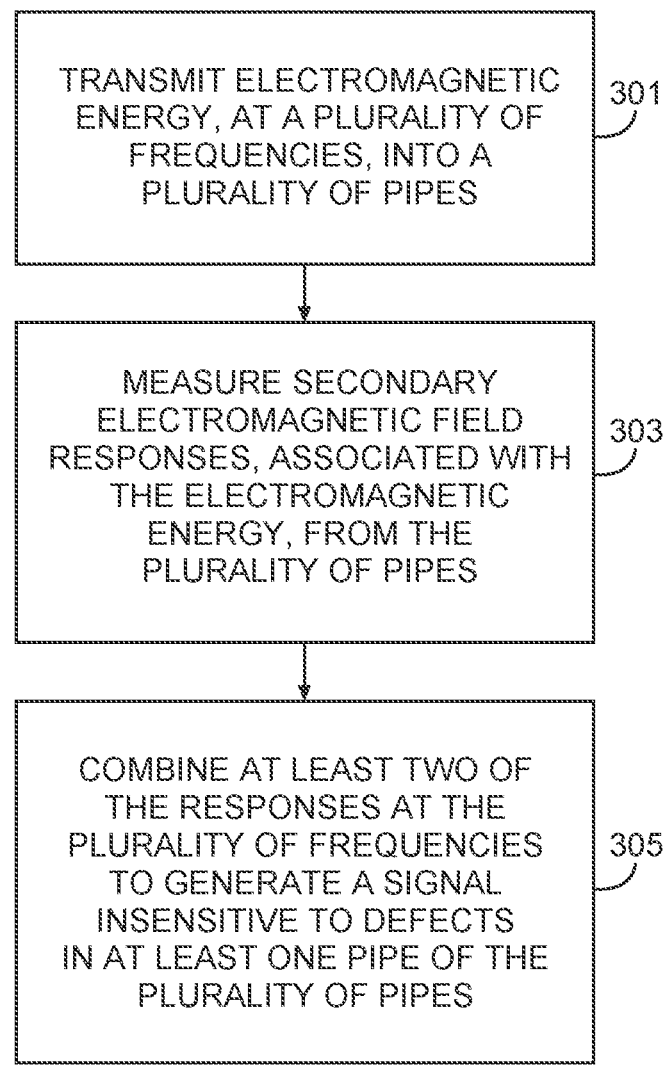
FIG. 3 is a flowchart of a method for selective pipe inspection, according to various examples of the disclosure.

FIG. 3 is a flowchart of a method for selective pipe inspection, according to various examples of the disclosure. In block 301, electromagnetic energy, at a plurality of frequencies, is transmitted into a plurality of pipes. In an example, the plurality of electromagnetic waves are transmitted into a plurality of concentric pipes. The plurality of electromagnetic waves may comprise N frequencies transmitted into M concentric pipes where N>M. The range of frequencies may be determined based on a radial depth of concentric pipes to be inspected. The plurality of frequencies may be determined based on a total thickness of the concentric pipes to inspect.

In block 303, secondary electromagnetic field responses, associated with the electromagnetic energy, are measured from the plurality of pipes. In block 305, at least two of the responses at the plurality of frequencies are combined, using the above calculated cancellation coefficients (i.e., weights), to generate a signal that is insensitive to defects in at least one pipe of the plurality of pipes. The signal may be insensitive to defects of a predetermined size and the defects may comprise variations in thickness, relative magnetic permeability, or electrical conductivity of the at least one pipe. The block may include combining at least N of the plurality of frequencies to generate the signal that is insensitive to defects in M pipes of the plurality of pipes, wherein M is equal or less than N−1, as noted previously.

The method may further determine the secondary electromagnetic response from a joint of a drill string or downhole tool and determine a cancellation coefficient that reduces the secondary electromagnetic response from that joint. Additionally, features of the plurality of pipes may be determined in response to the measurement of the electromagnetic response from the joint or from simulation results.

Figure 4:
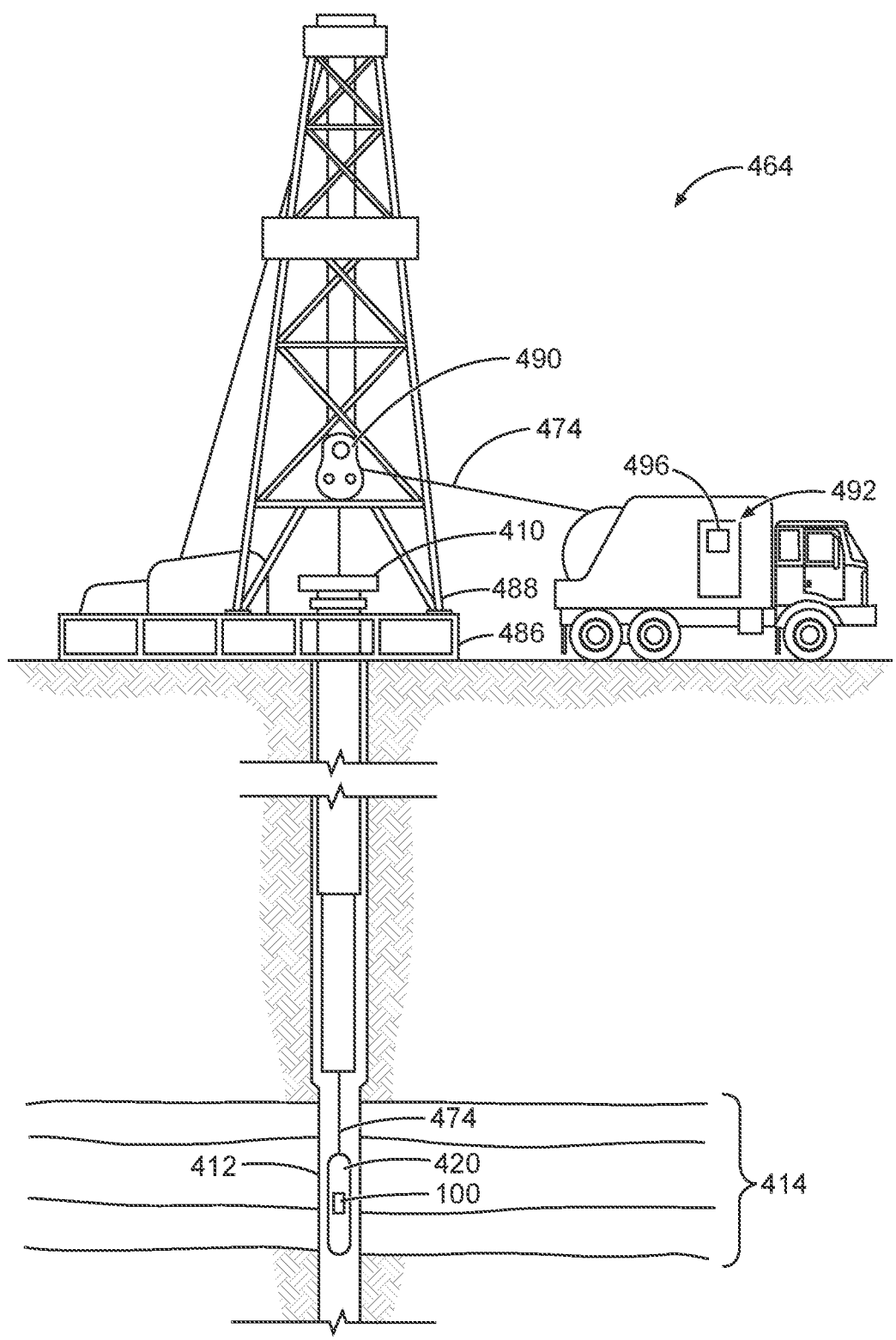
FIG. 4 is a diagram showing a wireline system, according to various examples of the disclosure.

FIG. 4 is a diagram showing a wireline system 464, according to various examples of the disclosure. The system 464 may comprise at least one wireline logging tool body 420, as part of a wireline logging operation in a borehole 412, including the inspection tool 100 as described previously.

A drilling platform 486 equipped with a derrick 488 that supports a hoist 490 can be seen. Drilling oil and gas wells is commonly carried out using a string of drill pipes connected together so as to form a drillstring that is lowered through a rotary table 410 into the borehole 412. Here it is assumed that the drillstring has been temporarily removed from the borehole 412 to allow the wireline logging tool body 420, such as a probe or sonde with the inspection tool 100, to be lowered by wireline or logging cable 474 (e.g., slickline cable) into the borehole 412. Typically, the wireline logging tool body 420 is lowered to the bottom of the region of interest and subsequently pulled upward at a substantially constant speed.

During the upward trip, at a series of depths, the inspection tool 100 may be used to inspect the pipes of the borehole 412. The resulting data may be communicated to a surface logging facility (e.g., workstation 492) for processing, analysis, and/or storage. The workstation 492 may have a controller 496 that is able to execute any methods disclosed herein. The workstation 492 may include modules comprising hardware circuitry, a processor, and/or memory circuits that may store software program modules and objects, and/or firmware, and combinations thereof that are configured to execute the method of FIGS. 2 and 3 as instructions.

In an example, the inspection tool 100 may be used to transmit an electromagnetic field and then measure the resulting secondary electromagnetic field responses generated by the pipes being inspected. The resulting data may be transmitted to the surface workstation 492 via telemetry. The workstation 492, with its controller 496, may process that telemetry, execute any methods disclosed herein, and generate a two-dimensional image of the downhole pipes.

Figure 5:
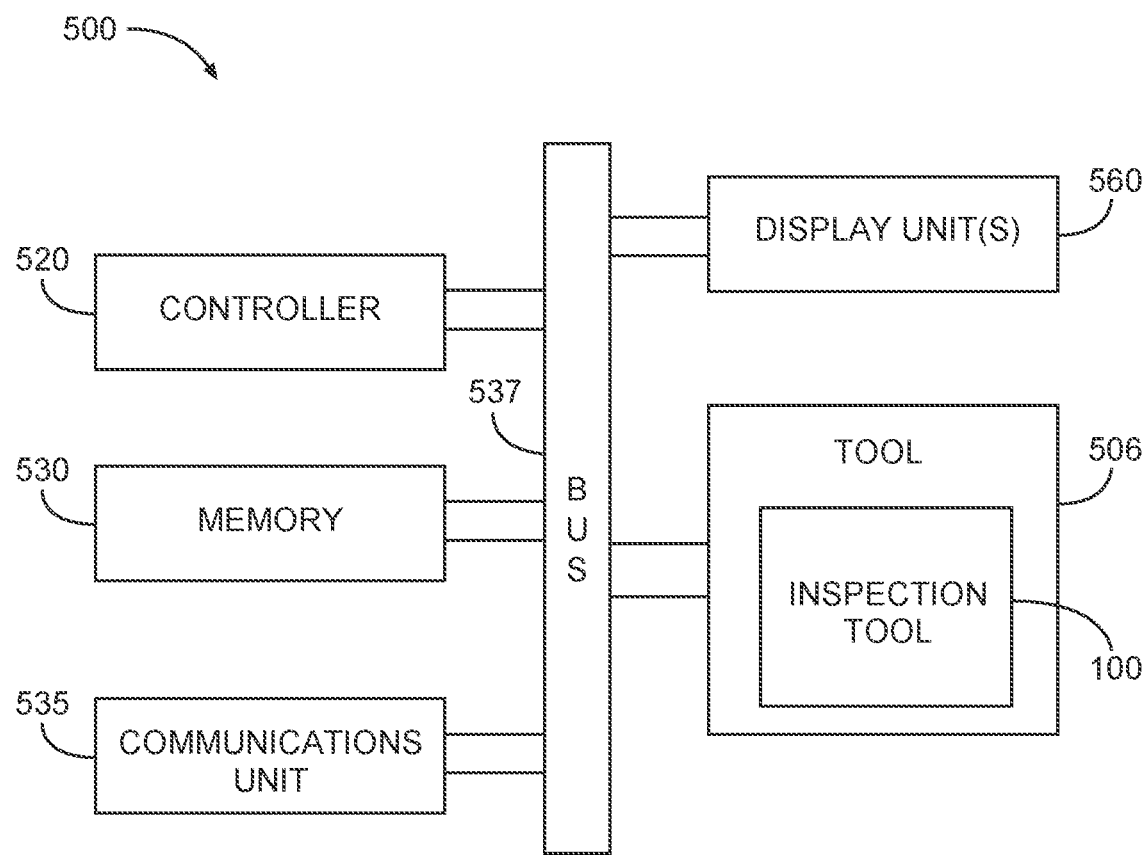
FIG. 5 is a block diagram of an example system operable to implement the activities of multiple methods, according to various examples of the disclosure.

FIG. 5 is a block diagram of an example system 500 operable to implement the activities of multiple methods, according to various examples of the disclosure. The system 500 may include a tool housing 506 having the inspection tool 100 disposed therein. The system 500 may be implemented as shown in FIG. 4 with reference to the workstation 492 and controller 496.

The system 500 may include circuitry such as a controller 520, a memory 530, and a communications unit 535. The memory 530 may be structured to include a database. The controller 520, the memory 530, and the communications unit 535 may be arranged to operate as a processing unit to control operation of the inspection tool 100 and execute any methods disclosed herein in order to determine the condition of borehole pipes.

The communications unit 535 may include communications capability for communicating from downhole to the surface or from the surface to downhole. Such communications capability can include a telemetry system such as mud pulse telemetry. In another example, the communications unit 535 may use combinations of wired communication technologies and wireless technologies.

The system 500 may also include a bus 537 that provides electrical conductivity among the components of the system 500. The bus 537 can include an address bus, a data bus, and a control bus, each independently configured or in an integrated format. The bus 537 may be realized using a number of different communication mediums that allows for the distribution of components of the system 500. The bus 537 may include a network. Use of the bus 537 may be regulated by the controller 520.

The system 500 may include display unit(s) 560 as a distributed component on the surface of a wellbore, which may be used with instructions stored in the memory 530 to implement a user interface to monitor the operation of the tool 506 or components distributed within the system 500. The user interface may be used to input parameter values for thresholds such that the system 500 can operate autonomously substantially without user intervention in a variety of applications. The user interface may also provide for manual override and change of control of the system 500 to a user. Such a user interface may be operated in conjunction with the communications unit 535 and the bus 537.

These implementations can include a machine-readable storage device having machine-executable instructions, such as a computer-readable storage device having computer-executable instructions. Further, a computer-readable storage device may be a physical device that stores data represented by a physical structure within the device. Such a physical device is a non-transitory device. Examples of machine-readable storage devices can include, but are not limited to, read only memory (ROM), random access memory (RAM), a magnetic disk storage device, an optical storage device, a flash memory, and other electronic, magnetic, and/or optical memory devices.

Figure 6:
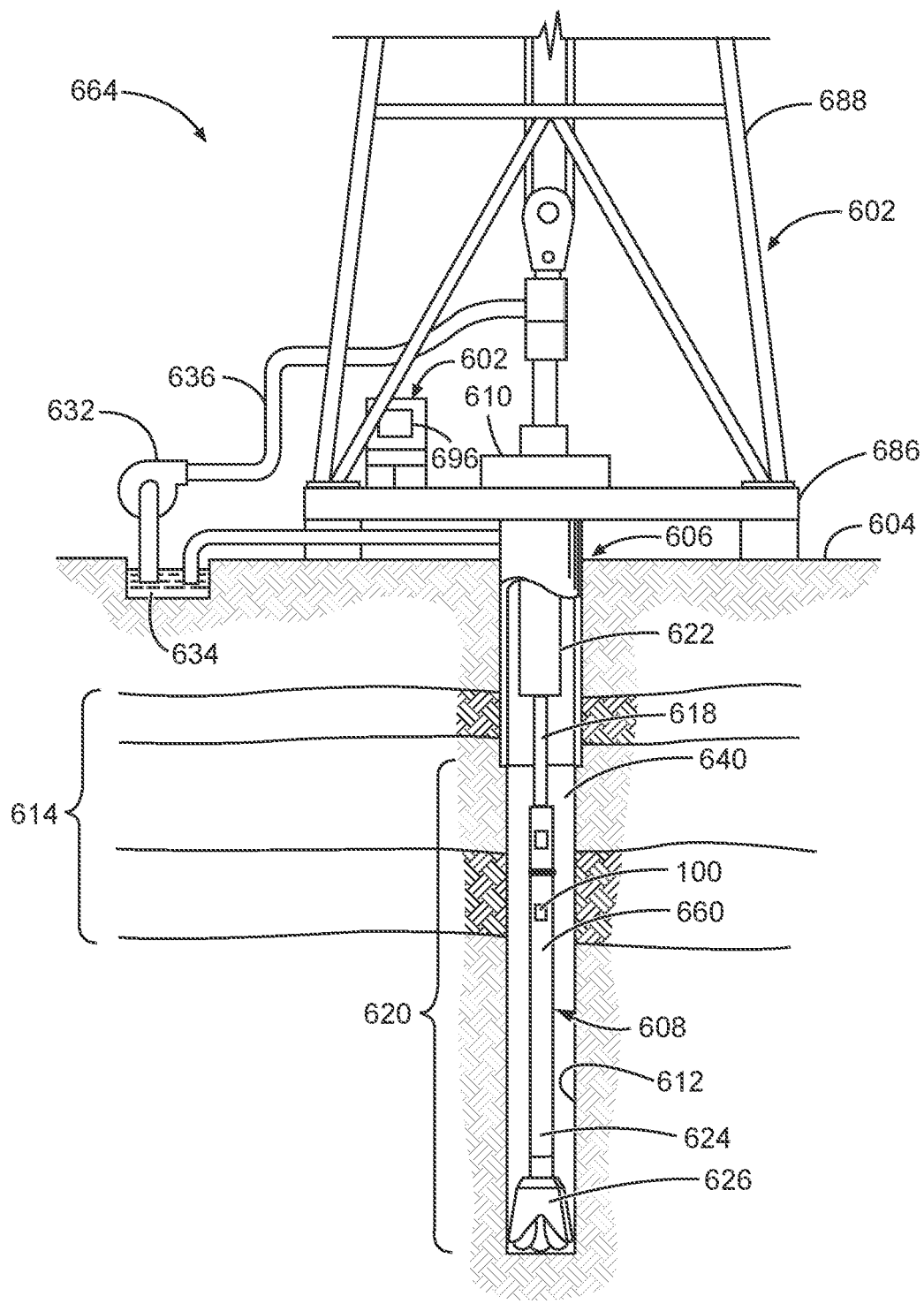
FIG. 6 is a diagram showing a drilling system, according to various examples of the disclosure.

FIG. 6 is a diagram showing a drilling system 664, according to various examples of the disclosure. The system 664 includes a drilling rig 602 located at the surface 604 of a well 606. The drilling rig 602 may provide support for a drillstring 608. The drillstring 608 may operate to penetrate the rotary table 610 for drilling the borehole 612 through the subsurface formations 614. The drillstring 608 may include a drill pipe 618 and a bottom hole assembly (BHA) 620 (e.g., drill string), perhaps located at the lower portion of the drill pipe 618.

The BHA 620 may include a MWD/LWD tool 660, including an inspection tool 130, and a drill bit 626. The drill bit 626 may operate to create the borehole 612 by penetrating the surface 604 and the subsurface formations 614. The inspection tool 100 may be used to determine a condition of pipes that are located in the borehole 612 as described previously.

During drilling operations within the borehole 612, the drillstring 608 (perhaps including the drill pipe 618 and the BHA 620) may be rotated by the rotary table 610 and/or by the mud motor 690 that is located down hole. The drill collars 622 may be used to add weight to the drill bit 626. Drill collars 622 may also operate to stiffen the BHA 620, allowing the BHA 620 to transfer the added weight to the drill bit 626, and in turn, to assist the drill bit 626 in penetrating the surface 604 and subsurface formations 614.

During drilling operations within the borehole 612, a mud pump 632 may pump drilling fluid (sometimes referred to as "drilling mud") from a mud pit 634 through a hose 636 into the drill pipe 618 and down to the drill bit 626. The drilling fluid can flow out from the drill bit 626 and be returned to the surface 604 through an annular area 640 between the drill pipe 618 and the sides of the borehole 612. The drilling fluid may then be returned to the mud pit 634, where such fluid is filtered. In some examples, the drilling fluid can be used to cool the drill bit 626, as well as to provide lubrication for the drill bit 626 during drilling operations. Additionally, the drilling fluid may be used to remove subsurface formation cuttings created by operating the drill bit 626.

A workstation 692 including a controller 696 may include modules comprising hardware circuitry, a processor, and/or memory circuits that may store software program modules and objects, and/or firmware, and combinations thereof that are configured to execute the method of FIGS. 2 and 3 as instructions.

In an example, the inspection tool 100 may be used to transmit an electromagnetic field and then measure the resulting secondary electromagnetic field responses generated by the pipes being inspected. The resulting data may be transmitted to the surface workstation 692 via telemetry. The workstation 692, with its controller 696, may process that telemetry, execute any methods disclosed herein, and generate a two-dimensional image of the downhole pipes.

Example 1 is a method comprising: transmitting electromagnetic energy, at a plurality of frequencies, into a plurality of pipes; measuring secondary electromagnetic field responses, associated with the electromagnetic energy, from the plurality of pipes; calculating weights using pipe information or the secondary electromagnetic field responses; combining a plurality of the responses using the weights, at the plurality of frequencies, to generate a signal insensitive to a subset of the pipes or defects in at least one pipe of the plurality of pipes; and determining a feature of the at least one pipe of the plurality of pipes based on the signal.

In Example 2, the subject matter of Example 1 can further include adjusting the weights such that the signal is insensitive to defects of a predetermined size.

In Example 3, the subject matter of Examples 1-2 can further include wherein the defects comprise variations in thickness of the at least one pipe, variations in relative magnetic permeability or the at least one pipe, or variations in electrical conductivity of the at least one pipe.

In Example 4, the subject matter of Examples 1-3 can further include wherein determining the feature of the at least one pipe comprises comparing the signal to a library of functions or a forward simulation model.

In Example 5, the subject matter of Examples 1-4 can further include wherein the defects comprise variations in electrical conductivity of the at least one pipe.

In Example 6, the subject matter of Examples 1-5 can further include wherein combining at least two of the responses comprises combining at least N of the plurality of frequencies to generate the signal, through adjustment of the weights, that is insensitive to defects in M pipes of the plurality of pipes, wherein M is equal or less than N−1.

In Example 7, the subject matter of Examples 1-6 can further include wherein combining at least two of the responses comprises combining at least N of the plurality of frequencies to generate the signal through adjustment of weights that is insensitive to M pipes of the plurality of pipes, wherein M is equal or less than N−1.

In Example 8, the subject matter of Examples 1-7 can further include wherein transmitting the electromagnetic energy comprises transmitting the electromagnetic energy into a plurality of concentric pipes.

In Example 9, the subject matter of Examples 1-8 can further include wherein the plurality of frequencies is determined based on a total thickness of concentric pipes to inspect.

In Example 10, the subject matter of Examples 1-9 can further include wherein transmitting the electromagnetic energy, over the plurality of frequencies, comprises transmitting the electromagnetic energy over N frequencies into M concentric pipes, wherein N>M.

In Example 11, the subject matter of Examples 1-10 can further include: determining a secondary electromagnetic response from a joint; and
adjusting the weights to reduce the secondary electromagnetic response from the joint.

In Example 12, the subject matter of Examples 1-11 can further include wherein the weights are subsequently used in a section of well without the joint.

Example 13 is an apparatus comprising: a transmitter to transmit electromagnetic energy, over a plurality of frequencies, into a plurality of pipes; a receiver to receive secondary electromagnetic wave responses, associated with the electromagnetic energy, from the plurality of pipes; and circuitry coupled to the receiver to generate a signal, combine at least two of the responses at a plurality of frequencies to generate a signal that is insensitive to defects of at least one of the pipes of the plurality of pipes, and determine at least one feature of the plurality of pipes based on a comparison of the signal to a library of signals or a simulation model.

In Example 14, the subject matter of Example 13 can further include a second transmitter to transmit the plurality of electromagnetic waves.

In Example 15, the subject matter of Examples 13-14 can further include at least one additional receiver disposed on the apparatus substantially symmetrically with respect to the transmitter.

In Example 16, the subject matter of Examples 13-15 can further include wherein the at least one additional receiver is disposed axially along the apparatus.

In Example 17, the subject matter of Examples 13-16 can further include wherein the circuitry is further to perform measurement of joints to generate pre-known features of the plurality of pipes.

Example 18 is a system comprising: an inspection tool comprising: a transmitter to emit electromagnetic energy, over a plurality of frequencies, into downhole pipes; and an axially distributed receiver to receive a plurality of secondary electromagnetic responses, associated with the electromagnetic energy, from the downhole pipes; and circuitry coupled to the inspection tool, the circuitry to generate a signal from a combination of a plurality of the responses, each response at a different frequency of the plurality of frequencies, wherein the signal is insensitive to defects of at least one pipe of the downhole pipes.

In Example 19, the subject matter of Example 18 can further include wherein the inspection tool is disposed in a wireline tool or a drill string tool.

In Example 20, the subject matter of Examples 18-19 can further include wherein the circuitry is further to determine known cancellation coefficients based on a joint and generate a library of pipe properties and determine properties of the selected pipe based on the library of pipe properties.

Although specific examples have been illustrated and described herein, it will be appreciated by those of ordinary skill in the art that any arrangement that is calculated to achieve the same purpose may be substituted for the specific examples shown. Various examples use permutations and/or combinations of examples described herein. It is to be understood that the above description is intended to be illustrative, and not restrictive, and that the phraseology or terminology employed herein is for the purpose of description. Combinations of the above examples and other examples will be apparent to those of skill in the art upon studying the above description.

What is claimed is:

1. A method comprising:
transmitting electromagnetic energy over N frequencies into M concentric pipes, wherein N>M;
measuring secondary electromagnetic field responses, associated with the electromagnetic energy, from the pipes, wherein said measuring secondary electromagnetic field responses includes determining a secondary electromagnetic response from a joint;
determining weights using property information for one or more of the pipes and the secondary electromagnetic field responses;
adjusting the weights to reduce the secondary electromagnetic response from the joint;
combining a plurality of the secondary electromagnetic field responses using the weights, at two or more of the frequencies, to generate a signal insensitive to property-based responses from a subset of the pipes; and
determining a defect of at least one of the pipes based on the signal.

2. The method of claim 1, further comprising adjusting the weights such that the signal is insensitive to defects of a predetermined size.

3. The method of claim 1, wherein the property-based responses include responses based on defects that comprise variations in thickness, relative magnetic permeability, or electrical conductivity of at least one of the subset of pipes.

4. The method of claim 1, wherein determining the feature of the at least one pipe comprises comparing the signal to a library of functions or a forward simulation model.

5. The method of claim 1, wherein the property-based responses include responses based on defects comprising variations in electrical conductivity of the at least one pipe.

6. The method of claim 1, wherein combining the plurality of the responses comprises combining responses corresponding to the N frequencies to generate the signal, through adjustment of the weights, that is insensitive to defects in M−1 of the M pipes.

7. The method of claim 1, wherein the N frequencies are determined based, at least in part, on a total thickness of two or more of the M concentric pipes.

8. The method of claim 1, wherein the weights are subsequently used in a section of well without the joint.

9. The method of claim 1, further comprising adjusting weights for the at least one of the pipes based on the determined feature.

10. An apparatus comprising:
a transmitter to transmit electromagnetic energy over N frequencies into M concentric pipes, wherein N>M;
a receiver to measure secondary electromagnetic field responses associated with the electromagnetic energy, from the pipes including determining a secondary electromagnetic response from a joint; and
circuitry coupled to the receiver to,
determine weights using property information for one or more of the pipes and the secondary electromagnetic field responses;
adjust the weights to reduce the secondary electromagnetic response from the joint;
combine at least two of the secondary electromagnetic field responses using the weights at a plurality of frequencies to generate a signal that is insensitive to responses of at least one of the pipes; and
determine at least one defect of the pipes based on a comparison of the signal to a library of signals or a simulation model.

11. The apparatus of claim 10, further comprising a second transmitter to transmit the electromagnetic energy.

12. The apparatus of claim 10, further comprising at least one additional receiver disposed on the apparatus substantially symmetrically with respect to the transmitter.

13. The apparatus of claim 12, wherein the at least one additional receiver is disposed axially along the apparatus.

14. The apparatus of claim 10, wherein the circuitry is further to perform measurement of joints to generate preknown features of the plurality of pipes.

15. A system comprising:
an inspection tool comprising:
a transmitter to emit electromagnetic energy, over a plurality of frequencies, into downhole pipes; and
a receiver axially offset from the transmitter to receive a plurality of secondary electromagnetic responses, associated with the electromagnetic energy, from a plurality of concentric downhole pipes including receiving a secondary electromagnetic response from a joint; and
circuitry coupled to the inspection tool, the circuitry configured to,
determine weights using property information for one or more of the downhole pipes and the secondary electromagnetic responses;
adjust the weights to reduce the secondary electromagnetic response from the joint;
combine at least two of the secondary electromagnetic responses using the weights at a plurality of frequencies to generate a signal that is insensitive to responses of at least one of the downhole pipes; and
determine at least one defect of the downhole pipes based on a comparison of the signal to a library of signals or a simulation model.

16. The system of claim 15, wherein the inspection tool is disposed in a wireline tool or a drill string tool.

17. The system of claim 15, wherein the circuitry is further to determine known cancellation coefficients based on a joint and generate a library of pipe properties and determine properties of a selected pipe based on the library of pipe properties.

\* \* \* \* \*